(12) United States Patent
Terada

(10) Patent No.: US 9,439,813 B2
(45) Date of Patent: Sep. 13, 2016

(54) FUNCTIONAL SHEET

(75) Inventor: Hirokazu Terada, Shiga (JP)

(73) Assignees: JNC CORPORATION, Tokyo (JP); JNC FIBERS CORPORATION, Tokyo (JP)

(*) Notice: Subject to any disclaimer, the term of this patent is extended or adjusted under 35 U.S.C. 154(b) by 0 days.

(21) Appl. No.: 13/333,975

(22) Filed: Dec. 21, 2011

(65) Prior Publication Data

US 2012/0164378 A1  Jun. 28, 2012

(30) Foreign Application Priority Data

Dec. 24, 2010 (JP) ................................ 2010-287974

(51) Int. Cl.
*B32B 3/10* (2006.01)
*A61F 13/513* (2006.01)

(52) U.S. Cl.
CPC ............ *A61F 13/51305* (2013.01); *B32B 3/10* (2013.01); *Y10T 428/24331* (2015.01)

(58) Field of Classification Search
CPC .................... A61F 13/511; A61F 13/51305
See application file for complete search history.

(56) References Cited

U.S. PATENT DOCUMENTS

| | | | |
|---|---|---|---|
| 5,763,044 A | 6/1998 | Ahr et al. | |
| 2003/0050615 A1* | 3/2003 | Sakamoto et al. | 604/358 |
| 2004/0267226 A1* | 12/2004 | Dabi et al. | 604/385.22 |

FOREIGN PATENT DOCUMENTS

| | | |
|---|---|---|
| GB | 896002 | 5/1962 |
| JP | 4342434 | 10/2009 |
| WO | WO 9856326 A1 * | 12/1998 |
| WO | 2004055262 | 7/2004 |

OTHER PUBLICATIONS

Machine Translation of JP 2006-183168.*
"Office Action of European Counterpart Application", issued on Mar. 26, 2014, p. 1-p. 4.
"Office Action of China Counterpart Application", issued on Dec. 18, 2015, p. 1-p. 12, with English translation thereof.
"Office Action of European Counterpart Application," issued on Feb. 18, 2016, pp. 1-5, in which the listed references were cited.
"Office Action of Taiwan Counterpart Application" with English translation, issued on Jun. 16, 2016, pp. 1-10.

* cited by examiner

*Primary Examiner* — Gerard Higgins
*Assistant Examiner* — Sathavaram I Reddy
(74) *Attorney, Agent, or Firm* — Jianq Chyun IP Office

(57) ABSTRACT

A functional sheet is described, in which a modifier is uniformly and exactly scattered and deposited such that sites where the modifier is deposited and sites where no modifier is deposited are clearly discriminated. The functional sheet is obtained by masking a surface of a sheet containing at least one fibrous layer on the surface by a planar object having a plurality of openings, applying a solution of a modifier from a side of the planar object, and allowing the modifier to deposit onto a whole surface of the sheet exposed to the openings of the planar object, and a functional sheet in which sites where the modifier is deposited form projections and sites where no modifier is deposited form plains in a surface fibrous layer of the functional sheet.

3 Claims, 1 Drawing Sheet

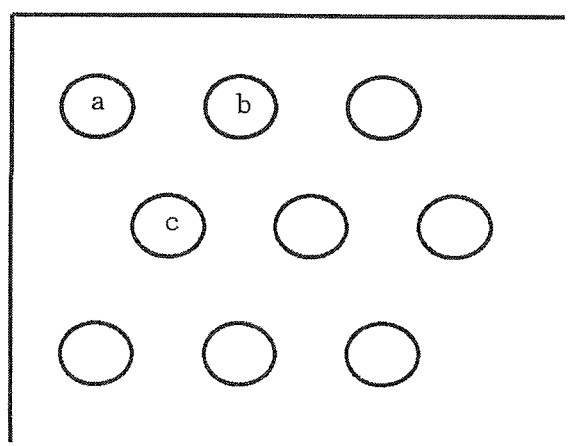

FUNCTIONAL SHEET

CROSS-REFERENCE TO RELATED APPLICATION

This application claims the priority benefits of Japan patent application serial no. 2010-287974, filed on Dec. 24, 2010. The entirety of the above-mentioned patent application is hereby incorporated by reference herein and made a part of specification.

TECHNICAL FIELD

The present invention relates to a functional sheet.

BACKGROUND ART

Conventionally, when a water-repelling function and a hydrophilic function or functionality of 2-methacryloyloxy-ethyl phosphorylcholine (MPC) polymer is imparted to a sheet or a nonwoven fabric, a method for adding a functional resin during melt extrusion in a process for manufacturing fibers or a technique for depositing a modifier onto a surface of the fibers according to a dipping method after processing into the fibers or the like is adopted in many cases. However, in the former case, an addition ratio or a processing temperature is frequently limited from an issue of thread breakage, and also a fluctuation in quality or a decrease in performance occurs by agglomeration of the modifier, or the like. Moreover, in the latter case, dropping of the modifier during carding or a change in performance in a heat treatment process or the like occurs in a subsequent process for processing into the nonwoven fabric. Thus, both cases are problematic.

The modifier is generally applied to a surface of the nonwoven fabric according to the dipping method after processing into the nonwoven fabric. However, in the case, allowing the modifier to uniformly deposit is possible onto a whole surface of the nonwoven fabric, but allowing the modifier to partially deposit thereonto is difficult.

A fibrous sheet having a surface uneven structure in which projections are hydrophobic and recesses are hydrophilic is known by the patent literature No. 1. However, a method for applying a silicone-based oil (hydrophobic agent) is applied to the fibrous sheet such that a degree of hydrophilicity may be continuously increased from a top side of the projections toward a bottom of the projections. Therefore, a boundary between hydrophilic sites and hydrophobic sites is unclear, and a function of the hydrophobic sites is restricted.

CITATION LIST

Patent Literature

Patent literature No. 1: JP 4342434 B

SUMMARY OF INVENTION

Technical Problem

A subject of the invention is to provide a functional sheet obtained by partially depositing a modifier.

Solution to Problem

The inventors of the invention have diligently continued to conduct research for solving the problem, as a result, have found that a sheet containing a fibrous layer is masked by using a planar object having a plurality of openings to allow a modifier to deposit onto a sheet region exposed to the openings, thereby allowing the modifier to uniformly and exactly scatter onto the sheet. The inventors have also found that the art is suitable particularly in a case of allowing the modifier to selectively, uniformly and exactly deposit only onto sites in which scattered convexes are formed, and thus the problem can be solved. Therefore, the inventors have completed the invention based on the knowledge.

The invention concerns a functional sheet, obtained by masking a surface of a sheet containing at least one fibrous layer on the surface by using a planar object having a plurality of openings and applying a solution of a modifier from a side of the planar object to allow the modifier to deposit onto a whole surface of the sheet exposed to the openings of the planar object.

The invention has the following constitutions.

Item 1. A functional sheet, obtained by masking a surface of a sheet containing at least one fibrous layer on the surface by using a planar object having a plurality of openings and applying a solution of a modifier from a side of the planar object to allow the modifier to deposit onto a whole surface of the sheet exposed to the openings of the planar object.

Item 2. The functional sheet according to the item 1, wherein an opening area of a single hole of the planar object having a plurality of openings is in the range of approximately 0.75 to approximately 175 $mm^2$.

Item 3. The functional sheet according to any one of the items 1 or 2, wherein a method for applying the solution of the modifier is to spray the solution of the modifier or to apply the solution of the modifier by using a contact roll.

Item 4. The functional sheet according to any one of the items 1 to 3, wherein the fibrous layer is a fibrous web or a nonwoven fabric.

Item 5. The functional sheet according to any one of the items 1 to 4, wherein sites where the modifier is deposited form projections and sites where no modifier is deposited form plains in a surface fibrous layer.

Item 6. The functional sheet according to the item 5, obtained by pressing the planar object having a plurality of openings onto the fibrous layer on the surface of the sheet, allowing the plains to form in parts of the fibrous layer onto which the planar object is pressed, allowing the projections to form in parts of the fibrous layer corresponding to the openings of the planar object, and allowing the modifier to deposit onto the surface of the sheet exposed to the openings of the planar object.

Advantageous Effects of Invention

A modifier is uniformly and exactly scattered and deposited on a sheet of the invention. Moreover, in particular, the modifier is selectively, more uniformly and exactly deposited only on sites in which scattered convexes are formed. The modifier is uniformly deposited on the sites where the modifier is deposited to have a low fluctuation of deposition concentration, and deposition of the modifier can be substantially completely blocked onto sites where the deposition of the modifier is not intended. Therefore, the sites where the modifier is deposited and the sites where no modifier is deposited are clearly discriminated (the sites where the modifier is deposited and the sites where no modifier is deposited coexist with a boundary), and thus a difference in functionality is more clearly developed with easiness. Advantageous effects being different from effects caused by a sheet in which the modifier is uniformly deposited over a whole surface of the sheet are developed. Simultaneously, the advantageous effects are high, in particular, when parts where the modifier is deposited form projections.

BRIEF DESCRIPTION OF DRAWINGS

FIG. 1 is a diagram showing one example of a planar object having a plurality of openings.

DESCRIPTION OF EMBODIMENTS

In the invention, a sheet is masked by allowing a planar object having a plurality of openings to closely contact with the sheet and allowing a modifier to deposit onto the sheet through the openings to obtain the sheet on which the modifier is partially deposited.

Specific examples of the sheets include a fibrous layer such as a fibrous web, a nonwoven fabric and a woven fabric, a laminate obtained by laminating two or more kinds of the fibrous layers selected therefrom or a laminate obtained by laminating a film with at least one kind of the fibrous layers. In order to form convexes as described later, the sheet preferably has stress deformation properties. The fibrous web or the nonwoven fabric is particularly preferred.

Any method for allowing the modifier to deposit onto the sheet may be optionally employed if a solution of the modifier is uniformly applied. Specifically, a method for spraying the solution of the modifier or a method for applying the solution of the modifier with a contact roll is employed. Specific examples of the methods for spraying the solution include a spray method for applying pressure from a nozzle having a narrowed pore diameter to a liquid to discharge the liquid. Specific examples also include a method for applying the modifier with a contact roll onto which the solution of the modifier is impregnated. If the modifier is deposited according to the methods, the sites where the modifier is uniformly deposited can be formed on parts corresponding to the openings when masking the sheet, and a boundary between the sites where the modifier is deposited and sites where no modifier is deposited becomes clear.

A shape of the openings of the planar object is not particularly limited. Specific examples include a round hole, an elliptical hole, a square hole, a polygonal hole and a rhombic hole. Arrangement of the openings is not particularly limited and the openings may be optionally arranged in parallel, zigzag or the like. An opening area of a single hole is preferably in the range of approximately 0.75 to approximately 175 mm$^2$, further preferably, in the range of approximately 1.5 to approximately 20.0 mm$^2$ in view of uniform deposition of the modifier. An opening ratio of the openings of the planar object in the sites onto which the modifier is allowed to deposit is preferably in the range of approximately 5 to approximately 90%, further preferably, in the range of approximately 10 to approximately 80% in view of a deposition ratio for the modifier to be deposited.

The planar object may be planar at least in parts in which the modifier is allowed to deposit onto the sheet through the planar object, and thus a rotating member having a plurality of openings on the surface can be used.

For example, a rotating roll is used as the rotating member. From an upper surface of the sheet to be carried by a conveyer, the rotating roll having a plurality of openings and rotating at an identical speed is applied to the sheet to allow the modifier deposit onto the sheet exposed from the openings through the rotating roll.

Upon applying the planar object having a plurality of openings to the upper surface of the sheet, the planar object may be pressed onto a surface of the sheet. The planar object is pressed thereonto, and thus the convexes can be easily formed on the surface of the sheet corresponding to the openings. The modifier is to be deposited onto the projections.

Specific examples of fibers constituting the fibrous layer include synthetic fibers (fibers including polyethylene, polypropylene, polyester, acryl, nylon and polyvinyl chloride), natural fibers (woody fibers), regenerated fibers (rayon) and semisynthetic fibers (acetate). When the synthetic fibers are used as the fibers, fibers including a thermoplastic resin are advantageous in processing (spinning and thermal bonding upon processing into the nonwoven fabric). Moreover, the synthetic fibers may be composite fibers including a plurality of resin ingredients (specific examples include composite fibers of polyethylene and polypropylene or composite fibers of polyethylene and polyester). Moreover, the fibers may be mixed fibers obtained by mixing the above fibers.

As a fibrous layer on which the convexes are easily formed, the fibrous web or the nonwoven fabric is preferred. Hereinafter, a method for forming the convexes on the sheet by pressing the planar object having a plurality of openings onto an upper surface of the nonwoven fabric will be explained, but is not limited thereto.

Nonwoven's unit weight of a web to be used for manufacturing the nonwoven fabric is preferably in the range of approximately 15 to approximately 50 g/m$^2$, particularly preferably, in the range of approximately 20 to approximately 35 g/m$^2$ in view of clearly forming the projections on the nonwoven fabric. Moreover, a specific volume is preferably in the range of approximately 20 to approximately 70 cm$^3$/g, particularly preferably, in the range of approximately 25 to approximately 60 cm$^3$/g in view of bulkiness.

Moreover, the web to be used in the invention may be a laminate with any of other layers, such as a fibrous layer, a sheet and a film, in the range without adversely affecting properties for imparting an uneven shape, processability and other desired advantageous effects of the invention.

In order to manufacture a nonwoven fabric in which entangled points between fibers are thermally bonded by allowing hot air to pass through a web containing thermally bondable fibers, an ordinary hot-air processing machine (suction band dryer) can be used and hot-air processing treatment can be performed under conditions to be ordinarily applied. In general, according to the hot-air processing machine, while hot air having a predetermined temperature is blown to the web supplied on a self-propelled conveyer net, hot air coming through the web is sucked from a bottom of the conveyer net. Thus, the hot-air processing machine is suitable for processing the thermally bondable fibers into a bulky nonwoven fabric.

Temperature of hot air may be optionally selected if the temperature is sufficient for the thermally bondable fibers to thermally bond with each other on the entangled points. Hot-air treatment is preferably performed at temperature higher by approximately 1 to approximately 10° C. relative to a melting point of a resin ingredient constituting the thermally bondable fibers. Moreover, when the composite fibers are used as the thermally bondable fibers, the hot-air treatment is preferably performed in the range of temperature higher by approximately 1 to approximately 5° C. relative to a melting point of a resin ingredient having a low melting point, and lower by approximately to approximately 30° C. than a melting point of a resin ingredient having a high melting point in view of bulkiness.

A nonwoven fabric having a surface uneven structure is obtained by pressing the planar object having a plurality of openings onto at least one surface of the nonwoven fabric in which the entangled points between fibers are thermally bonded by hot air, and then removing the planar object. The uneven shape may be formed by pressing a flat plate having a plurality of openings as the planar object. In view of operability, however, the uneven shape is preferably formed by allowing the nonwoven fabric to pass through at least one rotating roll having a plurality of openings on the surface Pressing time is not particularly limited if the time is sufficient for projections and recesses to be formed. When using at least one rotating roll having a plurality of openings on the surface, specific examples of rotational speed of the roll include the range of approximately 1 to approximately 100 meters per minute without being particularly limited thereto.

Pressure upon pressing the planar object having a plurality of openings onto the nonwoven fabric can be optionally selected if the pressure is sufficient to allow the uneven shape to form and at a level where the recesses are not excessively collapsed by taking a shape, properties and so forth of the nonwoven fabric into consideration. The pressure is preferably in the range of approximately 0.098 MPa to approximately 2.0 MPa. The pressure is further preferably in the range of approximately 0.2 to approximately 1.0 MPa in view that the recesses are not excessively collapsed.

According to pressing treatment using the planar object having a plurality of openings, melting equal to or more intensive than melting during the thermal bonding to be performed according to the hot-air treatment in a previous process is preferably avoided for the nonwoven fabric. However, such consideration is needed that a structure of the recesses formed by being compressed by the pressing treatment does not return to a state before pressing by means of the planar object. For the purpose, the planar object preferably has heat at a level where the nonwoven fabric does not thermally melt, more specifically, heat at which the thermal bonding of the nonwoven fabric does not further progress during the pressing treatment. Although the planar object having a plurality of openings is not needed to be warmed during the pressing treatment, the pressing treatment is preferably performed while the nonwoven fabric has remaining heat of the hot-air treatment in the previous process. When warming the planar object having a plurality of openings (when remaining heat of the nonwoven fabric is not sufficient, or when performing the pressing treatment after the nonwoven fabric becomes cold), the planar object may be warmed to temperature at a level where the nonwoven fabric does not generate thermal melting of the fibers during the pressing treatment. Temperature of the nonwoven fabric in the case is preferably approximately 50° C. or higher, and lower by approximately 5° C. or more than a melting point of the thermally bondable fibers (a melting point of an ingredient having a low melting point when the composite fibers are used as the fibers). Furthermore, temperature where the recesses are not excessively collapsed is preferably approximately 60° C. or higher, and lower by approximately 10° C. or more than the melting point of the thermally bondable fibers. The temperature is particularly preferably in the range of approximately 70° C. or higher, and lower by approximately 20° C. or more than the melting point of the thermally bondable fibers. If temperature for warming the nonwoven fabric is decreased to a level lower by approximately 5° C. or more than the melting point of the thermally bondable fibers, the temperature is sufficient to prevent less bulky plains from being pressed into a film.

Moreover, if the temperature is approximately 50° C. or higher, the less bulky plains do not return to the state before pressing the planar object, and the temperature is sufficient for the nonwoven fabric to hold a clear uneven structure. In addition, "the planar object is warmed" includes a case where remaining heat of the web is transferred to the planar object during the pressing treatment onto the web, as a result, the planar object is sufficiently heated for forming an uneven structure to the nonwoven fabric.

The planar object used when performing the pressing treatment is not particularly limited if the planar object has the openings, for example, the planar object may have not only the roll shape as described above but also a plate shape. The planar object may be set in an outlet of the hot-air processing machine, and also in any place in a subsequent process. The temperature of the nonwoven fabric during performing the pressing treatment of the nonwoven fabric by using the planar object is preferably in the range as described above. In terms of energy efficiency, pressing processing is preferably performed by utilizing own heat of the nonwoven fabric without positively heating the planar object. In the case, a distance from the outlet of the hot-air processing machine to an inlet of a pressing processing machine (planar object) is set under conditions in which the temperature of the nonwoven fabric is maintained.

In the planar object having a plurality of openings, various shapes can be adopted for individual openings, such as a round hole, a square hole, a hexagonal hole, a long round hole, a longicorn hole, a rhombic hole, a round cross-shaped hole and a cross-shaped hole, without being limited thereto. An opening area of a single hole is preferably in the range of approximately 0.75 to approximately 150 mm$^2$, and the arrangement thereof can be optionally selected, such as openings arranged in parallel or a zigzag pattern or without regularity. The openings arranged in the zigzag pattern are preferred in view of tenacity of the nonwoven fabric.

As shown in FIG. 1, "arranged in the zigzag pattern" means a pattern to be perforated at a predetermined pitch at least in three directions such that the nearest three upper openings a, b and c form apexes of a substantially equilateral triangle, without being particularly limited thereto.

When the planar object having a plurality of openings is used, the openings form bulky hills and a continuous surface between the openings forms the less bulky plains on an uneven nonwoven fabric obtained. An opening ratio of the openings of the planar object in sites in contact with the nonwoven fabric is preferably in the range of approximately 5 to approximately 90%, further preferably, in the range of approximately 10 to approximately 80%. In order to obtain a more flexible nonwoven fabric, an area of the less bulky plains may be decreased. The opening ratio may be optionally changed according to an application and a purpose.

A material of the planar object is not particularly limited as long as the material can withstand the warming and a load such as the pressing pressure as described above. Specific examples include stainless steel (SUS) or aluminum, and SUS can be preferably used in view of heat resistance and pressure resistance. Thickness and size of the planar object are not particularly restricted.

Nonwoven's unit weight of the nonwoven fabric having the surface uneven structure is preferably in the range of approximately 15 g/m$^2$ to approximately 60 g/m$^2$, further preferably, in the range of approximately 15 g/m$^2$ to approximately 50 g/m$^2$, further more preferably, in the range of approximately 15 g/m$^2$ to approximately 30 g/m$^2$.

Moreover, thickness of the nonwoven fabric having the surface uneven structure is not particularly limited. The thickness (maximum thickness) of the thickest sites (projections) is preferably in the range of approximately 0.5 to approximately 5 mm. Moreover, a difference in height between the projections and adjacent recesses on at least one surface is preferably in the range of approximately 0.4 to approximately 5 mm. An art according to the invention has one feature in which properties for forming the uneven shape to a particularly bulky web are excellent. As a result, a relatively thick and bulky nonwoven fabric having a large difference between the projections and the recesses can be efficiently obtained.

A formed member may be formed by laminating and uniting any of other layers with the nonwoven fabric having the surface uneven structure in the range without adversely affecting the advantageous effects of the invention of the application. Any of other layers includes a fibrous layer containing woody fibers such as cotton and hemp, natural fibers, semisynthetic fibers such as rayon and acetate, synthetic fibers such as polyolefin, polyester, acryl, nylon and polyvinyl chloride, a sheet and a film. In the case, any of other layers may be united on a side of an uneven surface of the nonwoven fabric having the surface uneven structure or on the other surface. Specific examples of uniting methods include a needle punching method and a water entangling method without being limited thereto.

As the rotating member having a plurality of openings on the surface, in addition to the rotating roll as described above, an endless belt can also be used. Specifically, the endless belt having a plurality of openings on the surface is used, and the sheet is placed on the endless belt to deposit the modifier onto the sheet through the belt on the way of conveying the sheet, more specifically, to apply the modifier by means of spraying or using the contact roll to allow the modifier to uniformly scatter and deposit onto the sheet without decreasing productivity.

As the endless belt, a steel belt can be used, for example. A material to be used for the steel belt is preferably rust resistant even after spraying or applying the modifier or undeformable also in a heat treatment process such as drying. Specific examples include stainless steel (SUS) or aluminum, in particular, SUS 630 is preferably used from heat resistance, anti-rust properties and processability.

In addition, as the steel belt having a plurality of openings, a steel belt (made by KBK Steel Products Co. Ltd., for example) is processed to have openings by using a laser cutting method or a punching method, and thus used as the steel belt. Moreover, as the endless belt, a sheet conveyer made of Teflon (registered trademark), a fluorine-containing resin belt or the like may be adopted. A belt made by opening the above belt according to any method can be used.

Hereinafter, a case where the steel belt is used as the planar object having a plurality of openings will be specifically explained, but is not limited thereto.

An opening ratio is not particular defined, but is preferably approximately 70% or less, further preferably, approximately 50% or less from an issue of strength of the steel belt. If the opening ratio is high, sufficient welding cannot be performed on a plane for jointing and connecting the steel belt, resulting in insufficient connection strength to cause deformation by an external force or heat.

As a shape of the openings, a round hole, an elliptical hole, a quadrilateral hole, a polygonal hole, a rhombic hole or the like to be arranged in parallel or zigzag is selected. In particular, the shape arranged in zigzag is preferred from the issue of strength of the steel belt.

When the fibrous web or the nonwoven fabric is used as an original sheet, a steel belt having optionally produced openings can be used as a substitute for the conveyer net of a hot-air circulation heat treatment machine. In the case, an increase in the opening ratio is needed at a degree where penetration of hot air is not adversely affected, and the opening ratio is in the range of approximately 20 to approximately 70%, further preferably, in the range of approximately 30 to approximately 50%. When the opening ratio is approximately 20% or more, a degree of penetration of hot air is sufficient, hot air circulates, and therefore temperature is easily controlled. Moreover, hot air does not become turbulent on the steel belt, and thus the web on the conveyer is not disarranged.

When the steel belt is used as the substitute for the conveyer net of the hot-air circulation heat treatment machine, a web made by using thermally bondable composite fibers is placed on the steel belt having optionally produced openings, subjected to the hot-air treatment, and thus the nonwoven fabric can be obtained, for example. Moreover, an increase in an amount of circulating hot air generates pressing action to the web located on the openings of the steel belt to allow the convexes to be formed on a side of the surface of the nonwoven fabric in a direction of travel of hot air. The modifier is preferably deposited onto parts of the convexes through the steel belt.

As a method for depositing (applying) the modifier, an original sheet onto which the modifier is desirably deposited is placed on the steel belt having optionally produced openings to allow the modifier deposit onto the sheet from a side opposite to the sheet, namely, through the steel belt, by spraying the modifier or by means of the contact roll. For example, when a sheet showing hydrophilicity is placed on the steel belt, and a water-repelling liquid is sprayed and deposited through the steel belt having optionally produced openings, water-repelling parts are to be scattered on sites corresponding to the optionally produced openings relative to a hydrophilic nonwoven fabric.

Thus, the modifier being different from a modifier ordinarily deposited on a whole surface of the original sheet (a fiber treating agent in a case of fibers, for example) is allowed to optionally scatter and deposit onto the sheet, and thus a sheet utilizing functionality of each modifier can be obtained.

When the fibrous web is used as the original sheet, the nonwoven's unit weight of the web is preferably in the range of approximately 10 to approximately 200 $g/m^2$, particularly preferably, in the range of approximately 15 to approximately 100 $g/m^2$. Moreover, the specific volume is preferably in the range of approximately 20 to approximately 70 $cm^3/g$, particularly preferably, in the range of approximately 25 to approximately 60 $cm^3/g$ in view of bulkiness. In particular, when the convexes are formed by using hot air, the web is pressed onto the openings at an amount of hot air, and thus the convexes are formed. Thus, a high nonwoven's unit weight allows harder penetration of hot air through the web to cause harder pressing. Therefore, the nonwoven's unit weight is preferably in the range of approximately 10 to approximately 100 $g/m^2$, further preferably, in the range of approximately 10 to approximately 50 $g/m^2$.

As for the hot-air treatment, an ordinary hot-air processing machine (suction band dryer) can be used, and hot-air processing treatment can be performed under conditions to be ordinarily applied. The temperature of hot air may be optionally selected if the temperature is sufficient for the thermally bondable fibers to thermally bond with each other on the entangled points. The hot-air treatment is preferably performed at temperature higher by approximately 1 to approximately 10° C. relative to a melting point of a resin ingredient constituting the thermally bondable fibers. Moreover, when the composite fibers are used as the thermally bondable fibers, the hot-air treatment is preferably performed in the range of temperature higher by approximately 1 to approximately 5° C. relative to the melting point of the resin ingredient having the low melting point, and lower by approximately 10 to approximately 30° C. than the melting point of the resin ingredient having the high melting point in view of bulkiness.

In particular, in order to form the convexes on the web or the nonwoven fabric placed on the openings of the steel belt on the side of the surface of the web or the nonwoven fabric in the direction of travel of hot air by the pressing action according to the hot-air treatment, an amount of circulation hot air is preferably to be set in the range of approximately 2 meters per second to approximately 10 meters per second.

As a method for forming the convexes on the sheet and allowing the modifier to deposit onto the convexes, a method for forming the convexes by using hot air while allowing the sheet to convey on the endless belt is preferably employed when greater emphasis is placed on flexibility and feeling. According to a method for forming the convexes by pressing the rotating roll having a plurality of openings onto the sheet, a somewhat hard feeling is provided in pressed sites. Both methods may be separately used, as needed, depending on a desired performance and application.

According to the method of the invention, the sheet in which the sites where the modifier is deposited are exactly controlled in advance can be effectively manufactured by selecting a specification on the openings of the planar object to be used, or the like. Moreover, non-openings are masked by the planar object upon allowing the modifier to deposit onto the sheet, and therefore the modifier is not deposited onto undesired sites, a region where the modifier is deposited and a region where no modifier is deposited are completely discriminated, and thus a difference in functionality between the sites where the modifier is deposited and the sites where no modifier is deposited becomes more significant. Then, particularly in a case of performing spray deposition, the modifier is allowed to uniformly deposit evenly in the region where the modifier is deposited. Therefore, the boundary between both regions becomes more clearly. Simultaneously, a difference in an amount of deposition in the region where the modifier is deposited is reduced, and thus the difference in functionality becomes more significant. In particular, according to the invention, the modifier is allowed to selectively deposit only onto the parts of the convexes of the sheet having the uneven shape, and uniformly and exactly deposit onto the sites. Therefore, advantageous effects that cannot be achieved from a sheet in which the modifier is simply partially deposited can be achieved conjointly according to a clear discrimination between the region where the modifier is deposited and the region where no modifier is deposited and a combination of forming the projections and the recesses.

As the sheet to be used as the original sheet, in addition to various nonwoven fabrics obtained according to a carding method, a meltblown method, a spunbond method, a needle punching method, a water jet method or the like, the sheet of the woven fabric or the film can also be used.

Specific examples of the modifiers include the water-repelling agent as described above and a hydrophilizinq agent, and also an MPC polymer (functions such as moisture absorbing and moisturizing properties, antistatic properties and stain-resistant properties are added), a moisturizer such as hyaluronic acid and collagen. In the invention, the modifier is not limited as long as the modifier can be sprayed in liquid or deposited by using the contact roll.

Moreover, various advantageous effects can be achieved by the combination. For example, when the water-repelling agent is scattered on the hydrophilic nonwoven fabric, the water-repelling parts suppress wetback under a situation where a liquid through hydrophilic parts backs to give a dry feeling on the surface of the nonwoven fabric. Therefore, a decrease in rash and an improvement in dry feeling are seen by using the sheet for a surface material or a second layer of a disposable diaper or a sanitary napkin. Moreover, when the MPC polymer is allowed to scatter and deposit onto the hydrophilic nonwoven fabric, advantageous effects such as absorbing blood from wound or reducing proliferation of bacteria are achieved by imparting the absorbing properties and the stain-resistant properties.

Hereafter, the invention will be explained in greater detail based on Examples, but the invention is in no way limited to the Examples.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

Method for Preparing a Web and a Nonwoven Fabric

Thermally fusible sheath-core composite fibers constituted of polyethylene (sheath) and polypropylene (core) (use of ESC 023 having 2.2 dtex×51 mm as ES Fiber, made by ES FiberVisions Co. Ltd.) were processed by using a miniature carding machine, and thus a web having a nonwoven's unit weight of 25 g/m² was prepared. In the following, the web was used in Examples and Comparative Examples.

Next, the web was thermally treated at a heat treatment temperature of 130° C. for 5 seconds by using a hot-air circulation heat treatment machine, and thus a nonwoven fabric was obtained. In the following, the nonwoven fabric was used in Example 1 and Comparative Examples.

Method 1 for Depositing a Modifier

A nonwoven fabric was placed on a steel belt having round holes with a diameter of 3 mm and a pitch of 5 mm as arranged in zigzag at 60°, a modifier was sprayed and applied to the nonwoven fabric through the steel belt, and complete drying was performed at an amount of circulation hot air of 1.5 m/s and a drying temperature of 80° C. for 5 seconds by using a hot-air circulation dryer. A sprayed amount was adjusted such that an amount of deposited modifier becomes 0.5% by weight. In addition, test spraying is performed by adding a coloring agent (paint) soluble in the modifier, and thus such a fact can be easily confirmed that sites where the modifier is deposited are formed in sites where the nonwoven fabric is not masked on a side of the steel belt, and exists with a boundary with sites where no modifier is deposited, and that an amount of applied modifier in the sites where the modifier is deposited is uniform.

Method 2 for Depositing a Modifier

A web was placed on a steel belt having round holes with a diameter of 3 mm and a pitch of 5 mm as arranged in zigzag at 60°, and the web was thermally treated at an amount of circulation hot air of 2.5 m/s and a heat treatment temperature of 130° C. for 5 seconds by using a hot-air circulation heat treatment machine and processed into a nonwoven fabric undulated in a round hole shape. Then, a modifier was sprayed and applied to the web through the steel belt to allow the modifier to deposit only onto undulated parts. A sprayed amount by using a sprayer was the same as the amount according to the method 1 for depositing the modifier. Then, complete drying was performed at an amount of circulation hot air of 1.5 m/s and at a drying temperature of 80° C. for 5 seconds by using a hot-air circulation dryer.

Method for Evaluation of Absorption

Evaluation of absorption was performed by using artificial menstrual blood as shown below.

A rate of absorption was measured according to an EDANA method (ERT 150.5-02 Liquid strike-through time (second)).

A wetback amount was measured according to an EDANA method (ERT 151.3-02 Coverstock-wetback).

A liquid area after passing a liquid of 3 ml was measured, and diffusibility was evaluated.

Herein, the EDANA method is described in a standard "STANDARD TEST METHODS FOR THE NONWOVENS INDUSTRY—NEW EDITION 2008" issued by European Disposables and Nonwovens Association (EDANA).

Method for Confirming Uniform Deposition

A red aqueous solution (Acid Red 18 (dye)) was applied to a sheet subjected to a partial water-repelling treatment. Undyed water-repelling parts were visually confirmed, and sites where a modifier (water-repelling agent) was deposited and sites where no modifier was deposited were confirmed to coexist with a boundary.

Example 1

A hydrophilic nonwoven fabric obtained by treating the nonwoven fabric as described above with a hydrophilic oil was used. A water-repelling agent was sprayed and applied to the nonwoven fabric according to the method 1 for depositing the modifier. As the water-repelling agent, a fluorine-based water-repelling agent was used as a solution of 3% by weight.

When deposition of the modifier was visually confirmed according to the method for confirming uniform deposition, such a fact was confirmed that only parts corresponding to openings of a steel belt used were not dyed, and only parts corresponding to non-openings were uniformly dyed to have hydrophilicity.

When evaluation of absorption was performed on the sheet, the nonwoven fabric having a very low wetback amount was obtained, and a dry feeling was sensed.

Example 2

A sheet obtained by laminating a water-repelling meltblown nonwoven fabric (EL-Fino made by Chisso Corporation) and a rayon spunlace was used. A hydrophilic agent was sprayed and applied to a surface of a meltblown nonwoven fabric according to the method 1 for depositing the modifier. As the hydrophilic agent, an anionic hydrophilic agent was used as a solution of 3% by weight.

When a state of the modifier deposited was visually confirmed according to the method for confirming uniform deposition, only a region corresponding to openings of a steel belt used was uniformly dyed for the surface of the meltblown nonwoven fabric, and thus the sheet was confirmed to have uniform hydrophilicity in the region. A region corresponding to non-openings was not dyed. Moreover, a side of the rayon spunlace was dyed red on a whole surface.

When evaluation of absorption was performed on the sheet, a liquid held in the rayon spunlace passed through only a surface applied by the hydrophilic agent to a surface of the meltblown nonwoven fabric, and thus a moderate moisturizing feeling and reduction of pasting were seen.

Example 3

A hydrophilic web obtained by treating the web as described above with a hydrophilic oil was used. A water-repelling agent was applied to the web according to the method 2 for depositing the modifier, and thus a nonwoven fabric having the water-repelling agent uniformly deposited on parts of convexes was obtained. As the water-repelling agent, a fluorine-based water-repelling agent was used as a solution of 3% by weight.

When a state of the modifier deposited was visually confirmed according to the method for confirming uniform deposition, a region corresponding to openings of a steel belt used forms the convexes, only the convexes which correspond to the openings were not dyed, and only a region corresponding to non-openings was uniformly dyed. Thus, the web was confirmed to have uniform hydrophilicity in the region.

When evaluation of absorption was performed on the sheet, the nonwoven fabric having a very low wetback amount was obtained, and a dry feeling was sensed.

Comparative Example 1

Relative to Example 1

When evaluation of absorption was performed on a hydrophilic nonwoven fabric obtained by treating the nonwoven fabric as described above with the hydrophilic oil without depositing the modifier thereonto, the wetback amount was very large and wetting was sensed.

Comparative Example 2

Relative to Example 3

The hydrophilic web obtained by treating the web as described above with the hydrophilic oil was processed in a manner similar to the method 2 for depositing the modifier, and thus an undulated nonwoven fabric was obtained. However, the modifier was not applied.

When evaluation of absorption was performed on the nonwoven fabric, the wetback amount was very large and wetting was sensed.

INDUSTRIAL APPLICABILITY

A functional sheet of the invention can be utilized for a topsheet or second sheet of a hygienic material, a cosmetic article such as a face mask and a medical article such as a medical gauze and a haemostatic tape.

TABLE 1

| | Nonwoven's unit weight g/m² | Thickness mm | Rate of absorption Second | Wetback amount g | Liquid area after passing a liquid cm² |
|---|---|---|---|---|---|
| Example 1 | 23.8 | 0.869 | 12.84 | 2.006 | 26.11 |
| Example 2 | 25.0 | 2.130 | 1.75 | 0.098 | 28.9 |
| Example 3 | 26.3 | 1.813 | 1.25 | 0.073 | 38.2 |
| Comparative Example 1 | 24.7 | 0.81 | 6.66 | 3.123 | 30.77 |
| Comparative Example 2 | 26.9 | 2.148 | 1.82 | 0.154 | 25.1 |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A functional sheet, comprising a sheet containing at least one fibrous layer, wherein the sheet is obtained by masking and pressing a surface of the at least one fibrous layer using a planar object having a plurality of openings, wherein convexes are formed in parts of the at least one fibrous layer which are exposed to the plurality of openings of the planar object and plains are formed in parts of the at least one fibrous layer onto which the planar object is pressed, applying a solution of a modifier from a side of the planar object to allow the modifier to deposit onto whole surfaces of the convexes of the sheet and then removing the planar object, wherein portions of the at least one fibrous layer where the modifier was deposited are the convexes and portions of the at least one fibrous layer where no modifier was deposited are the plains, an area of each opening of the plurality of openings of the planar object is in the range of approximately 1.5 mm² to approximately 20 mm², and the modifier comprises a 2-methacryloyloxyethyl phosphorylcholine (MPC) polymer, a hyaluronic acid, or a collagen.

2. The functional sheet according to claim 1, wherein a method for applying the solution of the modifier is to spray the solution of the modifier or to apply the solution of the modifier by using a contact roll.

3. The functional sheet according to claim 1, wherein the at least one fibrous layer is a fibrous web or a nonwoven fabric.

* * * * *